Figure 1:
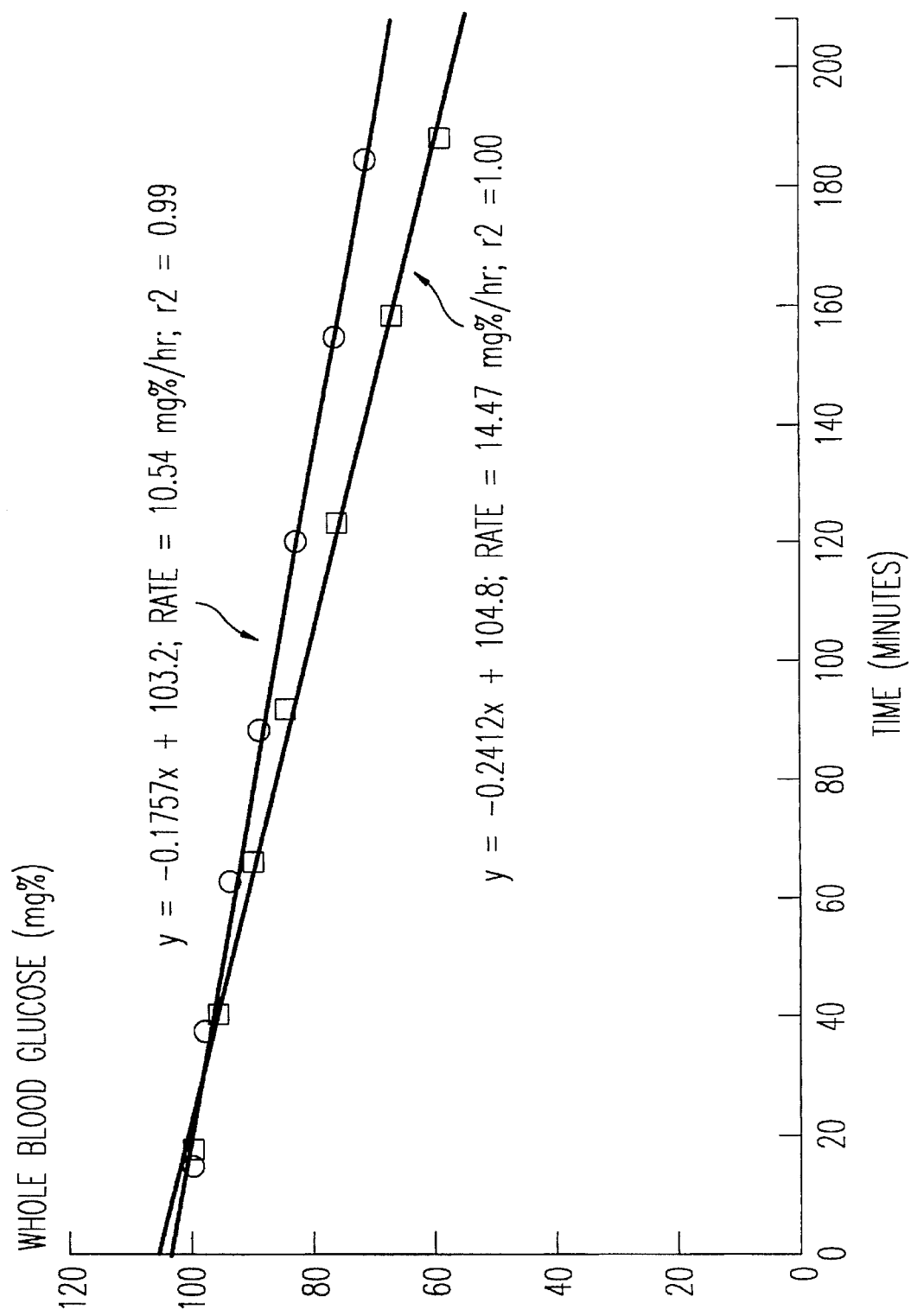

United States Patent [19]

Nierman et al.

[11] Patent Number: 5,529,907

[45] Date of Patent: Jun. 25, 1996

[54] METHOD OF DETERMINING PATIENT NEUTROPHIL ACTIVITY AND APPARATUS FOR PRACTICING THE SAME

[76] Inventors: David M. Nierman, 4444 E. 86th St., Apt. #20G, New York, N.Y. 10028; Thomas H. Kalb, 100 Carthage Rd., Scarsdale, N.Y. 10583

[21] Appl. No.: 182,826

[22] Filed: Jan. 19, 1994

[51] Int. Cl.$^6$ ............... C12Q 1/02; C12Q 1/00; C12M 1/34; G01N 33/49

[52] U.S. Cl. .............. 435/29; 435/4; 435/287.1; 435/287.9; 436/34; 436/43; 436/50; 436/51; 436/63; 436/174; 436/179; 436/180; 436/811

[58] Field of Search .................. 435/4, 29, 287, 435/291; 436/43, 50, 51, 63, 174, 179, 180, 34, 811; 424/9

[56] References Cited

PUBLICATIONS

Bone "Inhibitors of Complement & Neutophils: A Critical Evaluation of Their Role in The Treatment of Sepsis" Crit. Care Med. 20(6) 891–898 1992.
Bone et al. "Definitions for Sepsis & Organ Failure & Guidelines for the Use of Innovative Therapier Sepsis" Chest 101(6) 1644–1655 1992.
Nuijens, et al. "Plasma elastase, $\propto_1$–antitypsin, & Lactojerrin In Sepsis: Evidence for Neutrophils as Medlators In fatal Sepsis" J Lab Clin Med 199(2) 159–168 1992.
Baroso–Aranda et al. "Transformation of Neutrophils As Indicator of Irreversibility in Hemorrhagic Shock" Am. J. Physiol. 257 H846–H852 1989.
Rothe et al. "Flow Cytometric Parametrs of Neutrophil Function as Early Indicators of Sepsis or Trauma Related Pulomonery or Cardiovascular Organ Failure" J Lab Clin Med 115(1)52–61 1990.

*Primary Examiner*—Mindy Fleisher
*Assistant Examiner*—Nancy J. Degen
*Attorney, Agent, or Firm*—Oblon, Spivak, McClelland, Maier, & Neustadt

[57] ABSTRACT

The present invention relates to a method of determining the metabolic state of neutrophils present in the body of a patient. In particular, the present invention involves the measurement of the rates of in vitro glycolysis in blood samples taken from individuals as a function of the number of selected cells present in the blood sample, including neutrophils and red blood cells. The physiologic information provided by the present method, which, for example, indicates whether an individual's neutrophils are in a quiescent, primed or activated state, allows the medical practitioner to attain a better understanding of the patient's condition and, consequently, assists in the diagnosis and formulation of proper treatment.

28 Claims, 4 Drawing Sheets

METHOD OF DETERMINING PATIENT NEUTROPHIL ACTIVITY AND APPARATUS FOR PRACTICING THE SAME

1. FIELD OF THE INVENTION

The present invention relates to a method of determining the metabolic state of neutrophils present in the body of a patient. In particular, the present invention involves the measurement of the rates of in vitro glycolysis in blood samples taken from individuals as a function of the number of selected cells present in the blood sample. These rates and cell counts are then used in certain mathematical relationships to obtain numerical terms found to be probative of a patient's neutrophil metabolic state. An additional term, the delta value, is also generated which gauges the capacity of a patient's neutrophils to undergo stimulation by an exogenous agent. The delta value provides a further index of the metabolic activity of a patient's neutrophils independent from the neutrophil count. The physiologic information provided by the present method, which, for example, indicates whether an individual's neutrophils are in a quiescent, primed or activated state, allows the medical practitioner to attain a better understanding of the patient's condition and, consequently, assists in the diagnosis and formulation of proper treatment.

2. BACKGROUND OF THE INVENTION

2.1. Glucose Consumption in Whole Blood

The phenomenon of in vitro glycolysis of whole blood has been recognized since 1876 (26,30). A specimen of whole blood exhibits a decreasing amount of glucose over time due to ongoing glucose consumption in vitro by the blood cells (26). As technology has improved, attempts at quantifying this rate have yielded results ranging from 1.9 mg % per hour (44) to 5–10 mg % per hour at room temperature (43) and from 5–10 mg % per hour (35) to 10–20 mg % per hour at body temperature (29).

In vitro glycolysis does not occur in nonhemolyzed serum (27), is temperature dependent (28,29), is independent of the presence of insulin and the initial blood glucose level (25), and depends both on the numbers of blood cells and on their metabolic activity. In vitro, leukocytes, erythrocytes and platelets all continue to metabolize glucose as an energy source.

Neutrophils use $O_2$ to convert glucose to lactate through glycolysis, with hexokinase as the rate limiting step (38). A small amount, 2 to 3 percent, of the glucose metabolized is through the hexosemonophosphate shunt, the pathway that provides the NADPH needed to generate microbicidal oxidants and which pathway is "turned on" by phorbol myristate acetate (PMA). Lymphocytes also consume glucose, but with facilitated diffusion of glucose through the cell membrane instead of cell metabolic rate as the limiting step (39). Although the other white cell lines (monocytes, eosinophils, basophils) use glucose, the small numbers of these cells do not appear to impact significantly on the total amount consumed.

Erythrocytes use glucose through the glycolytic pathway and the hexosemonophosphate shunt. The metabolic dynamics and interactions are exceedingly complex, with many factors such as pH, lactate level, and accumulation of upstream metabolites having either stimulatory or inhibitory effects (40,41). PMA, however, does not change erythrocyte glucose utilization. Platelets use glucose depending on oxygen and glucose availability (42) and are stimulated by PMA.

In 1927, Falcon-Lesses showed that glycolysis rates were faster in whole blood from patients with leukemia than in normal blood (26). Since then, authors have described patients with leukemia (30), polycythemia (31,32) extreme eosinophilia (33) and leukocytosis (34) in whom this in vitro decrease in glucose concentration was so precipitous as to lead to very low glucose levels by the time of analysis—a condition called "artifactual hypoglycemia." On the other hand, Rawnsley and Bowman found that leukemic leukocytes consumed less glucose than normal leukocytes (35), suggesting that changes in leukocyte metabolism can also affect the amount of glucose consumed in vitro by a whole blood sample.

2.2. Neutrophil-Associated Host Autoinjury

Neutrophil-associated host autoinjury has been recognized as an important contributor to the endothelial damage that occurs in sepsis (1–9), adult respiratory distress syndrome or ARDS (5,10–13), multiple systems organ failure or MSOF (14–17), ischemia-reperfusion injury (18) and hemorrhagic shock (19). Neutrophils manifest a range of metabolic states—from normal quiescent cells (which derive their energy by anaerobic metabolism), to cells that have been primed by a variety of humoral mediators and that show an exaggerated response to a second activator (3), to fully activated cells. When activated, neutrophils undergo a series of marked metabolic changes in oxidative metabolism (the "respiratory burst"), characterized by a 50- to 100-fold increase in oxygen uptake, production of oxygen radical species (ROS), and the eventual degranulation of various neutrophil lysosomal enzymes (1,20,21). Primed neutrophils do not spontaneously display such activity, but show an enhanced response to activating stimuli with markedly augmented oxidative metabolism when compared to quiescent, non-primed cells. The neutrophil respiratory burst requires NADPH production, which is fueled by a large increase in glucose metabolism by way of the monophosphate shunt (20–22).

Respiratory burst capability, chemotaxis, spontaneous migration, chemiluminescence and direct superoxide anion production by neutrophils have been extensively investigated in sepsis (3,5). In particular, respiratory burst capability has been evaluated in sepsis, septic shock and longitudinally in septic shock (3,23). All these previous studies involved specialized analytical techniques using purified neutrophil preparations.

Circulating neutrophils become primed early in sepsis in the presence of circulating lipopolysaccharide and cytokines, including IL-1, TNF, IL-8, INF-λ, C5a, PAF and granulocyte colony stimulating factor. Compared to quiescent neutrophils, the additional stimulation of these primed neutrophils by either exogenous or endogenous agents causes many more of them to progress to respiratory burst. Paradoxically, neutrophils from patients who have progressed to septic shock show little response to additional exogenous stimulation (23), either because they are already maximally stimulated or because they have markedly depleted respiratory burst capability (1). It has been suggested that this diminished respiratory burst capability may be due to suppression by circulating humoral mediators (2). Serial neutrophil assays on patients who have survived septic shock have shown a return to normal function over time (2).

2.3. ROS as Markers for Neutrophil Metabolic State

The generation of ROS by neutrophils isolated from critically ill patients has been measured as a marker of neutrophil metabolic state. Evidence supporting in vivo priming of neutrophils during critical illness has been provided by measuring the generation of ROS by purified neutrophil isolates using either flow cytometry or spectrophotometry after an exogenous neutrophil stimulator (such as phorbol myristate 13-acetate (PMA) or N-formylmethionyl-leucyl-phenylalanine (FMLP)) is added (1,23). Opsonin receptor expression measured by chemiluminescence has also recently been used (24,25). These sophisticated laboratory techniques are time-consuming and expensive and require specialized expertise and equipment. Therefore, these methods are limited in their application to large scale use for either direct patient care or clinical research.

Hence, the determination of the metabolic state of a patient's neutrophils can provide invaluable information that is indicative of the condition of the patient and, in particular, may provide clues regarding the stage in which infection or disease has progressed. The amount of radical oxygen species generated by activated neutrophils, is obtained from purified neutrophil isolates requiring analytical techniques and sophisticated instruments not in general use. Thus, such techniques are severely limited and cannot be put into widespread use involving large numbers of patients. Furthermore, previous work done on in vitro glucose consumption in blood samples taken from ill patients had not established any demonstrable relationship between blood glucose consumption and neutrophil metabolic state. The difficulty of making measurements in whole blood is associated, in part, from the large number of cell types present in the blood which can affect the results of any measurement, as well as the large number of potentially interfering reactions taking place in the blood. In addition, certain phenomena, like the neutrophil respiratory burst, endure for only short periods, necessitating (as was widely held) purified cell preparations and sophisticated equipment and analytical techniques.

Thus, there remains a need for a method that can be made widely available to a great number of patients which provides information regarding the metabolic state of the neutrophils circulating in a patient's body. Such information can prove invaluable in the clinical setting and can lead to the identification of groups of patients who may best respond to a given treatment regimen. As described in greater detail below, with the information provided by the methods of the present invention, groups of patients manifesting clinical symptoms of non-sepsis, sepsis/severe sepsis, and patients in septic shock can be subcategorized further within each clinical group. With the substratification of such patients, those who may be at greatest risk or who may benefit the most from a particular prevention or treatment method may be identified expeditiously especially in those situations in which a proposed preventive/treatment regimen either is not widely accepted or requires a prophylactic or therapeutic agent that is not readily available.

3. SUMMARY OF THE INVENTION

Accordingly, the present invention is directed to a method that provides information regarding neutrophil activity in a given patient using techniques that are not unfamiliar to the clinician or laboratory blood specimen specialist and which techniques will provide results without the need for specialized, sophisticated instrumentation. In particular, it has now been found that glucose consumption in a sample of whole blood, namely, the rate of in vitro glycolysis, can be correlated directly to the metabolic state of a patient's neutrophils. Such correlations can be made with a high degree of confidence using experimentally-derived mathematical relationships that take into account the blood glucose consumption not just of neutrophil cells (pmn) but also red blood cells (rbc). Thus, by the methods of the present invention, a simple, reliable, readily available surrogate marker for neutrophil activity has been provided.

Other objectives of the present invention include providing a method of stratifying a population of patients according to the metabolic state of their neutrophils, predicting the propensity of a patient to suffer from a neutrophil-associated host autoinjury relative to a population of patients similarly at risk, and determining the initial glucose concentration in a blood sample at an initial time, $t_0$.

The present invention also contemplates an apparatus for determining the metabolic state of a patient's neutrophils, including automated embodiments that are capable of making multiple glucose measurements from a variety of native and exogenously stimulated blood samples, preferably at predesignated time intervals, as well as models capable of storing and processing data to arrive at the various numerical terms that are central to the practice of the present invention.

Other objects of the present invention will be apparent to the reader, particularly in light of the detailed description presented below.

4. BRIEF DESCRIPTION OF THE FIGURES

FIG. 1 shows a plot of the amount of glucose present in whole blood as a function of time in normal patients. The open circles denote results for native whole blood, while the open squares refer to results obtained from whole blood to which an exogenous neutrophil stimulator (i.e., PMA) had been added. Thus, for native whole blood, G (basal) was found to be 10.54 mg % per hour. For stimulated blood, G (stim) was 14.47 mg % per hour. (See, also, Equations 3 or $3_x$, below.)

Figure 2:
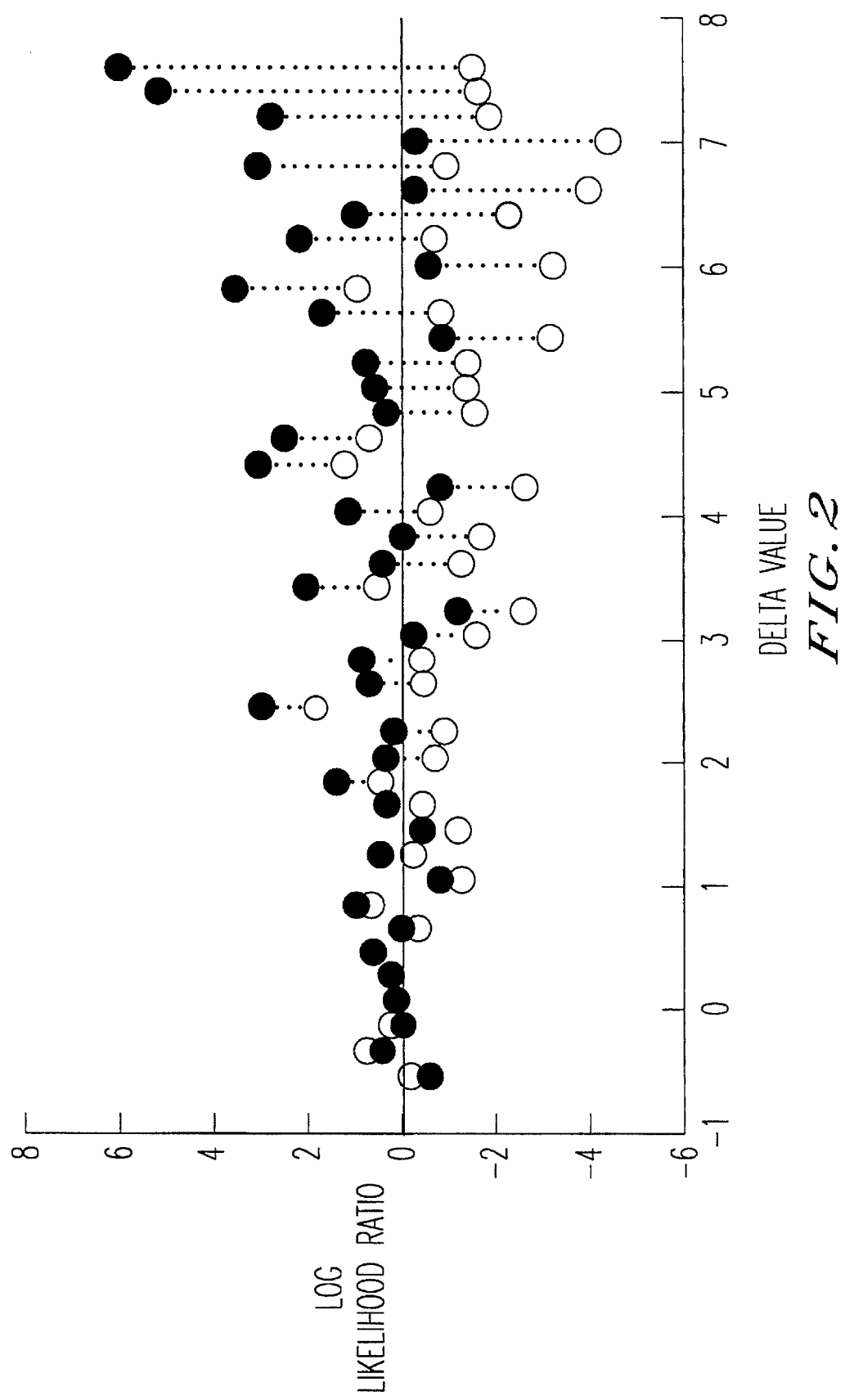

FIG. 2 illustrates a plot of the Log Likelihood Ratio or LLR obtained from normals (n=42). The open circles denote results from native whole blood, while the closed circles present results from whole blood treated with PMA. As shown by this plot, a negative LLR implies the absence of activated neutrophils (more open circles), whereas a positive LLR implies the presence of activated neutrophils (more closed circles). The difference between the matched pairs of open and closed circles is referred to as the delta value, plotted on the x-axis and which is a measure of the propensity of the neutrophils of a given individual to undergo exogenous stimulation by added neutrophil stimulant.

Figure 3:
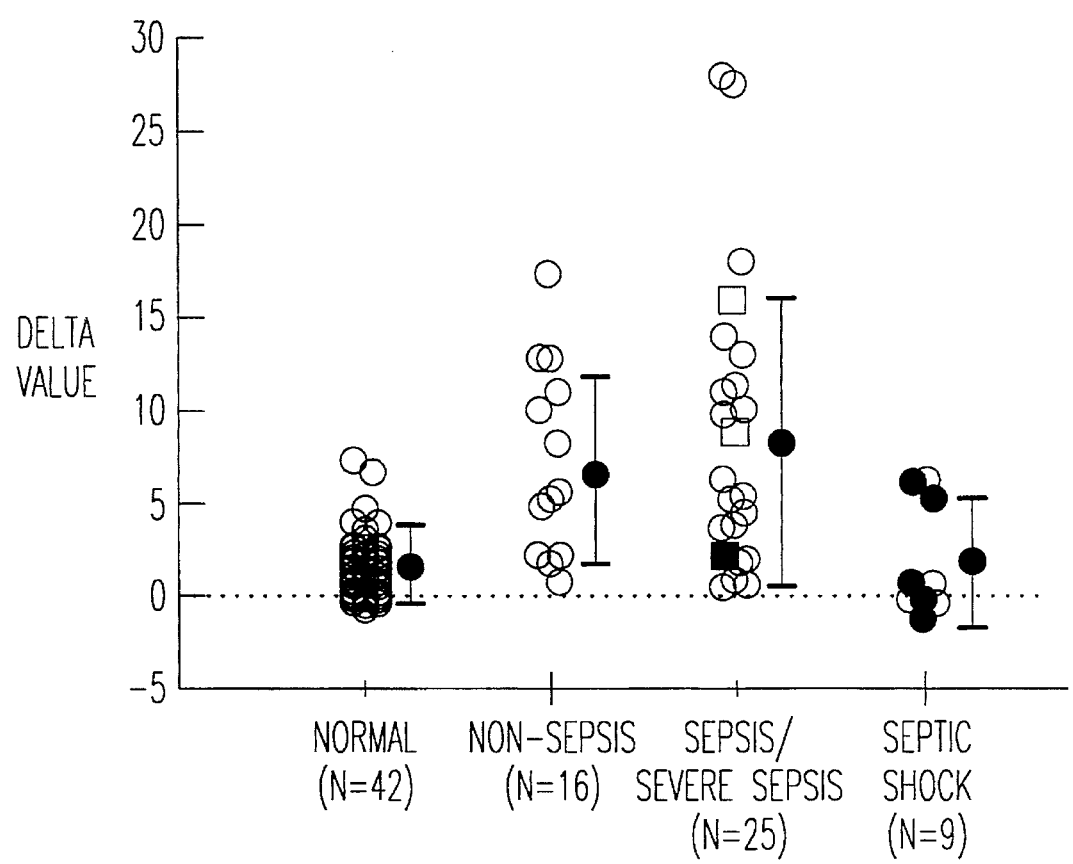

FIG. 3 shows the delta values found for groups of patients clinically categorized as normal, non-sepsis, sepsis/severe sepsis, and patients in septic shock. The closed circles represent septic deaths that occurred within 28 days of the delta assay: 2/25 or 8% of the sepsis/severe sepsis group and 5/9 or 56% of the septic shock group. Note that in the sepsis/severe sepsis category, the patients may be subdivided further into two subgroups having delta values falling either above or below the mean for the category, as a whole.

Figure 4A:
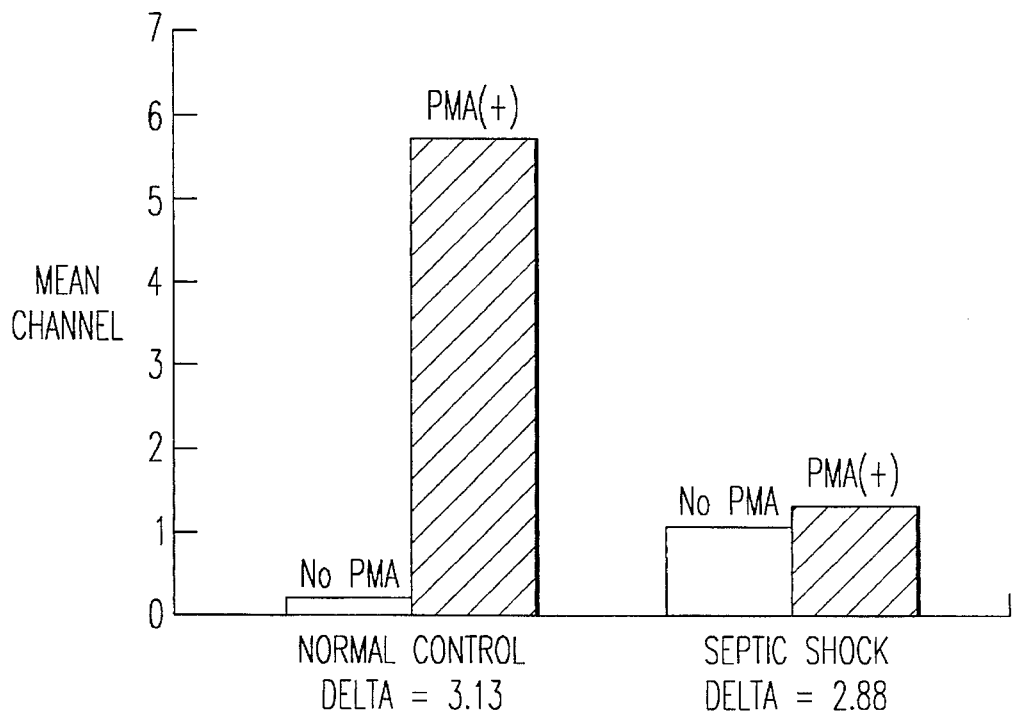
Figure 4B:
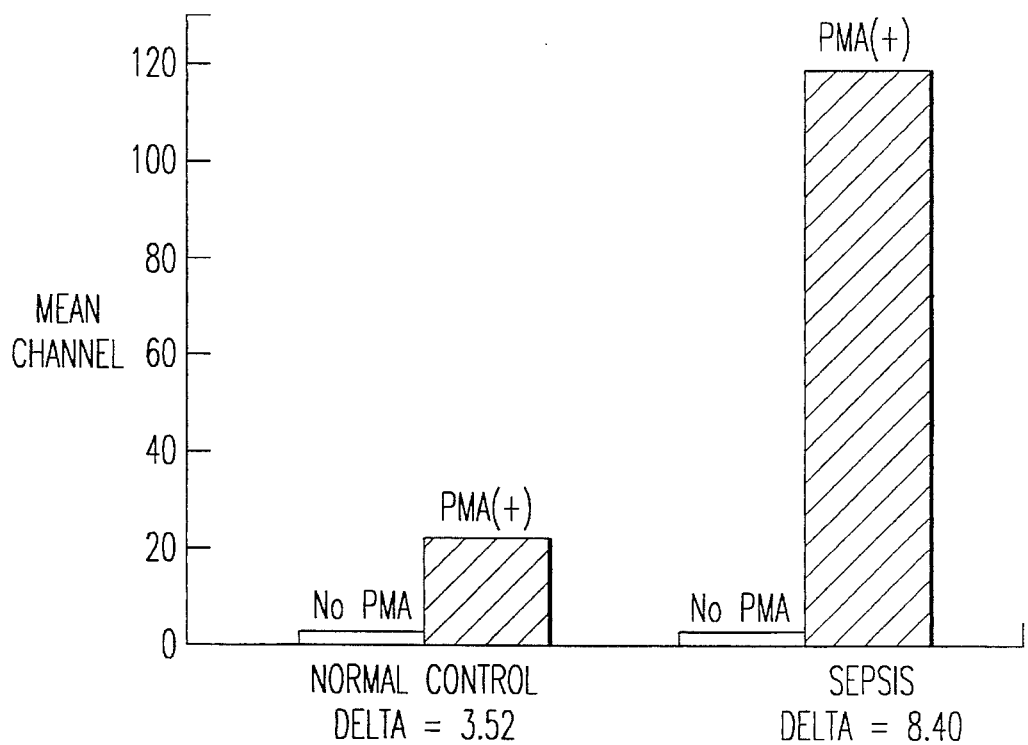

FIG. 4 presents a comparison of the results of the delta assay with the detection of ROS by flow cytometry. The top panel shows the histograms obtained by flow cytometry from a patient in septic shock. The bottom panel was obtained from a sepsis/severe sepsis patient (Note the larger scale for bottom panel). As indicated by the corresponding Δ values obtained by the present methods, patients in septic shock have neutrophils behaving similar to "normals", whereas sepsis/severe sepsis patients have "primed" neutrophils as evidenced by the large Δ value of 8.40.

5. DETAILED DESCRIPTION OF THE INVENTION

As described briefly above, the present invention is directed to methods for the determination of neutrophil activity in clinical patients, along with an apparatus suitable for the determination of same.

5.1. General Aspects of the Present Invention

Hence, according to one embodiment of the present invention, a method is disclosed of determining the metabolic state of a patient's neutrophils comprising: (a) measuring a patient's basal rate of glycolysis, red blood cell (rbc) count and neutrophil (pmn) count; (b) relating the measured basal rate of glycolysis with the patient's predicted basal and predicated stimulated rates of glycolysis to provide a log likelihood ratio (LLR), which ratio is an indication of the metabolic state of the patient's neutrophils, the predicted basal and predicted stimulated rates of glycolysis being derived from separate relationships established, respectively, from the measurement of the basal and stimulated rates of glycolysis of a population of normal individuals as a function of their rbc and pmn counts.

In another embodiment of the present invention, a method of determining the metabolic state of a patient's neutrophils is provided which comprises: (a) establishing a relationship, which is predictive of a basal rate of glycolysis as a function of red blood cell (rbc) count and neutrophil (pmn) count, by measuring the basal rates of glycolysis, rbc count, and pmn count of a population of normal individuals; (b) establishing a second relationship, which is predictive of a stimulated rate of glycolysis as a function of rbc count and pmn count, by measuring the stimulated rates of glycolysis, rbc count, and pmn count of a population of normal individuals whose neutrophils having been stimulated exogenously; (c) measuring a patient's basal rate of glycolysis, rbc count and pmn count; (d) calculating the patient's predicted basal and predicted stimulated glycolysis rates from the patient's rbc count and pmn count; and (e) relating the measured basal rate of glycolysis with the patient's predicted basal and predicted stimulated rates of glycolysis to provide a log likelihood ratio (LLR), which ratio is an indication of the metabolic state of the patient's neutrophils.

Generally, the predicted basal rate of glycolysis, $G_1$, is derived from the relationship (1), given below:

$$\text{Basal Rate } (G_1) = C_1 + (a_1 * pmn) + (b_1 * rbc) \qquad (1)$$

in which pmn and rbc are the measured pmn and rbc counts, respectively, and $C_1$, $a_1$, and $b_1$ are terms obtained from linear regression analysis. Specifically, $C_1$ is the constant or y-axis intercept of the regression line, $a_1$ is the x-coefficient of the independent variable pmn, and $b_1$ is the x-coefficient of the independent variable rbc. For the normal patient population used in this study, the value for $C_1$ was preferably 2.183, $a_1$ was preferably 0.000102, and $b_1$ was preferably 1.516.

Likewise, it has been found that the predicted stimulated rate of glycolysis, $G_2$, can be derived from the relationship (2), given below:

$$\text{Stimulated Rate } (G_2) = C_2 + (a_2 * pmn) + (b_2 * rbc) \qquad (2)$$

in which, again, pmn and rbc are the measured pmn and rbc counts, respectively. The other terms are as defined, above, for relationship (1). In the present study, $C_2$ was found to be preferably $-1.759$, $a_2$ was preferably 0.000755 and $b_2$ was preferably 2.354.

A third relationship, which provides the log likelihood ration (LLR) and which is important to the practice of the present invention, is given below:

$$LLR = [\{G - (G_1 + G_2)/2\} * \{G_2 - G_1\}] \div V \qquad (3).$$

In the relationship (3), G is the measured basal rate of glycolysis for the patient, $G_1$ is the predicted basal rate of glycolysis, $G_2$ is the predicted stimulated rate of glycolysis, and V is the square of the standard error of estimate. In the present study, the value of V has been found to be preferably 3.256.

The present invention also seeks to provide a method of stratifying a population of patients according to the metabolic state of their neutrophils comprising: (a) measuring a patient's basal and stimulated rates of glycolysis, red blood cell (rbc) count and neutrophil (pmn) count; (b) relating the measured basal rate of glycolysis with the patient's predicted basal and predicted stimulated rates of glycolysis to provide a first log likelihood ratio ($LLR_{basal}$); (c) relating the measured stimulated rate of glycolysis with the patient's predicted basal and predicted stimulated rates of glycolysis to provide a second log likelihood ratio ($LLR_{stim}$), the predicted basal and predicted stimulated rates of glycolysis being derived from separate relationships established, respectively, from the measurement of the basal and stimulated rates of glycolysis of a population of normal individuals as a function of their rbc count and pmn count; (d) subtracting the $LLR_{basal}$ from the $LLR_{stim}$ to provide an index, delta ($\Delta$), which is a measure of the propensity of the neutrophils of a given patient to undergo exogenous stimulation; (e) classifying patients of a given patient population into patient subgroups according to their $\Delta$ scores, to provide a stratification of the population of patients according to the metabolic state of their neutrophils. One useful classification may be placing patients in one group having delta values above the mean delta value and placing patients in another group having delta values below the mean delta value for the population, as a whole. Other classifications are apparent to those of ordinary skill in the art and may be based, for example, on the magnitude of delta, the age of the patient, clinical symptoms, medical history or combinations thereof.

Likewise, another embodiment of the present invention relates to a method of predicting the propensity of a patient to suffer from a neutrophil-associated host autoinjury, such as adult respiratory distress syndrome (ARDS), multiple systems organ failure (MSOF), reperfusion injury (e.g., associated with cerebral damage, post-myocardial infarction, ischaemic bowel), hemorrhagic shock, acute lung injury, and the like relative to a population of patients comprising: (a) measuring a patient's basal and stimulated rates of glycolysis, red blood cell (rbc) count and neutrophil (pmn) count; (b) calculating the predicted basal glycolysis rate, $G_1$; (c) calculating the predicted stimulated glycolysis rate, $G_2$; (d) determining the basal log likelihood ratio, $LLR_{basal}$, and stimulated log likelihood ratio, $LLR_{stim}$, from the measured basal and measured stimulated rates of glycolysis, respectively; (e) obtaining a delta value or $\Delta$ score for the patient from the values of $LLR_{basal}$ and $LLR_{stim}$, (f) comparing the patient's delta value or $\Delta$ score with the average of delta values obtained from a population of patients, a delta value that is significantly higher than the average being taken as an indication of a higher propensity of the patient to suffer from a neutrophil-associated host autoinjury relative to the population of patients. In certain embodiments of the invention, the population of patients is similarly at risk of suffering from a neutrophil-associated host autoinjury. By the same token, a delta value significantly below the average may be an indication that that patient may be more likely to suffer some other fate, such as septic death in patients classified as sepsis/severe sepsis.

In specific embodiments, patients in intensive care units may be stratified according to their clinical symptoms as normals, non-sepsis, sepsis/severe sepsis, and patients in septic shock. Within each category, subgroups of patients may be classified further according to their delta values, as described herein. The ability to classify patients in such subgroups may be important in identifying those patients who may benefit the most from a particular treatment regimen, e.g., those designed to treat or prevent the onset of ARDS or reverse the processes leading to septic death. Serial changes in the delta value of a patient undergoing treatment may also allow the quantifiable determination of the efficacy of a particular treatment regimen. Alternatively, such changes may be taken as a measure of the responsiveness or condition of individuals undergoing treatment.

According to yet another embodiment of the present invention, a method is disclosed for determining the initial glucose concentration in a blood sample at an initial time, $t_0$, comprising: (a) measuring a first glucose concentration in a blood sample at time, $t_1$; (b) repeating step (a) at least once at a subsequent time, $t_2$, to provide a second glucose concentration, the second glucose concentration being different from the first glucose concentration; (c) providing a substantially linear relationship between the glucose concentrations as a function of time; and (d) deriving the initial glucose concentration at initial time, $t_0$, from the linear relationship. In particular embodiments of the present invention step (a) is repeated in step (b) at least three times, preferably at least five times. Moreover, in preferred embodiments of the present invention, step (a) is repeated in step (b) every 15 minutes, most preferably, every 30 minutes. It is noted that the initial time, $t_0$, can be the time the blood sample was drawn.

The present invention also contemplates an apparatus for determining the metabolic state of a patient's neutrophils comprising: (a) a sensor capable of making multiple measurements of a patient's blood glucose; (b) a sensor capable of measuring a patient's rbc count; (c) a sensor capable of measuring a patient's pmn count; (d) a processor capable of relating a patient's measured glycolysis rate, rbc count, and pmn count to obtain a log likelihood ratio (LLR), based on the relationship (3), given below:

$$LLR=[\{G-(G_1+G_2)/2\}*\{G_2-G_1\}]\div V \quad (3)$$

in which G is the measured glycolysis rate for the patient, $G_1$ is the predicted basal rate of glycolysis, $G_2$ is the predicted stimulated rate of glycolysis, and V is the square of the standard error of estimate. In particular, the apparatus can be equipped with a processor capable of calculating a delta value ($\Delta$) based on the relationship (4), given below:

$$\Delta=LLR_{stim}-LLR_{basal} \quad (4)$$

in which $LLR_{stim}$ and $LLR_{basal}$ are log likelihood ratios obtained from the relationship ($3_x$), given below:

$$LLR_x=[\{G_x-(G_1+G_2)/2\}*\{G_2-G_1\}]\div V \quad (3_x)$$

in which $G_x$ is the measured glycolysis rate (wherein x is either basal or stimulated) for said patient, $G_1$ is the predicted basal rate of glycolysis, $G_2$ is the predicted stimulated rate of glycolysis, and V is the square of the standard error of estimate. In one embodiment of the present invention, the value of V is preferably 3.256.

Although a great many embodiments of the present apparatus can be contemplated, a preferred apparatus is capable of performing glucose measurements at preset time intervals automatically. Moreover, an apparatus of the present invention is preferably able to perform analyses on more than one blood sample at any given time. For example, one embodiment could be capable of making substantially simultaneous analyses on a native blood sample and an exogenously stimulated blood sample.

Other desirable features may include, but are not limited to, adding and mixing means for the introduction of at least one reagent for the exogenous stimulation of the neutrophils present in a blood sample. As will be further described below, such reagents may include, but are not limited to, phorbol myristate 13-acetate (PMA), N-formylmethionyl-leucyl-phenylalanine (FMLP), lipopolysaccharide (LPS), opsonized bacteria, interleukin-8, C3a, C5a, activated thrombin and the like.

Consistent with the objectives of the present invention, a number of indices has been developed which can distinguish patients whose neutrophils are metabolically activated from those whose neutrophils are quiescent. It was surprisingly found that such an index can be based on a comparison of the measured glycolysis rate of a whole blood sample with the expected glycolysis rates for activated or quiescent neutrophils, as a function of the cells present in the blood which have been found to contribute to the overall blood glycolysis. It was discovered that the most significant of these are neutrophils (pmn) and red blood cells (rbc).

5.2. Statistical Analysis

When a numerical indicator exhibits different distributions in two populations, the information carried by that indicator about which population an unidentified blood specimen belongs to can be expressed by the likelihood ratio statistic (48), or equivalently, its logarithm (LLR). Where the distribution in both populations is normal with common variance, the LLR can be calculated using a simple standard formula (See, immediately below). A positive LLR reflects glycolysis rates more likely to be found in specimens with activated neutrophils, whereas a negative LLR reflects glycolysis rates more likely to be found in specimens with quiescent neutrophils. The larger the magnitude of the LLR, the more diagnostic the observed glycolysis rate is of either the activated or quiescent state. LLRs near zero reflect specimens whose glycolysis rates lie in a region of overlap between activated and quiescent specimens and are relatively uninformative.

The data are presented as the mean±standard deviation. Multiple regression analysis was used to determine which cell types correlated with glycolysis rates. Group differences were analyzed by analysis of variance with Tukey's post hoc contrasts. A p value$\leq 0.05$ was considered to be statistically significant.

More particularly, all statistical calculations were performed using SYSTAT statistical software, version 5.0 (Evanston, Ill.). When a regression analysis is performed, for each case in the data set (i.e., each member of our "normal" data set), the actual measured value is compared to the predicted value. Additionally, a regression equation describing a regression line of the means is generated. The standard error of the estimate, V, is a measure of the variability of population members about this line of means. The standard error of the estimate, which mathematically describes the amount of variability around the mean, is related to the standard deviations of the dependent and the independent variables and the scope of the regression line of the means. Those values are derived from standard mathematical theory, and are automatically generated by the SYSTAT software, as were the regression equations.

The value of V and the predicted regression equations $G_1$ and $G_2$ were generated from our 52 normals. This sample of 42 normals was taken to be representative of the entire population of normals that exist. As would be apparent to those skilled in the art, however, it is certainly possible (even likely) that if a sample of 10,000 normals were studied, the values of the regression equations and V may differ. Such statistically-adjusted values, however, are within the scope of the invention and are consistent with its objectives.

5.3. Index of Granulocyte Reactive Oxygen Species Formation

An index of granulocyte reactive oxygen species formation was used to confirm pmn activation under similar conditions to those used to evaluate in vitro glucose utilization of PMA treated blood samples. Significant stimulation of granulocyte ROS formation was observed in PMA exposed blood samples compared to untreated samples (mean channel 63 vs. 171; percent fluorescence positive 4.7 vs. 19.3% respectively, p<0.02).

5.4. Determination of Glycolysis Rates and Cell Counts

Glycolysis rates were determined, first for normals.

Glucose measurements can be made using either chemical or enzymatic techniques. Chemical measurements, which depend on the reducing properties of glucose, are not very specific and are less preferred, except for the ortho-toluidine method. The ortho-toluidine method is based on the condensation of glucose with an aromatic amine and glacial acetic acid. The stable green color that develops is measured spectrophotometrically. This method also measures other aldose saccharides such as lactose, sucrose, fructose and maltose, and is very inaccurate in patients with uremia. The ortho-toluidine reagent is very toxic and corrosive.

Preferred methods are enzymatic, including the use of hexokinase, and glucose dehydrogenase.

The hexokinase method is the most specific, but the most expensive. This method uses the following reactions:

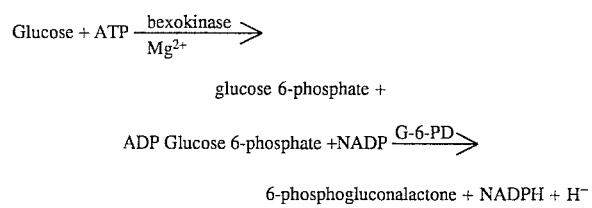

The glucose dehydrogenase is the most recently developed method. This reaction is very specific for beta-D-glucose, and uses NAD and mutarotase as auxiliary enzymes to reduce the reaction time.

The most commonly used and, perhaps, preferred method is the glucose oxidase method, used in the Examples below. The initial reaction is the following:

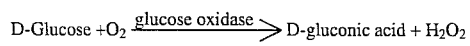

This reaction is quantitated either manometrically (wherein glucose is determined by measuring the rate of oxygen consumed using an oxygen electrode, and the $H_2O_2$ formed is removed by catalase and iodide plus molybdate without yielding oxygen) or calorimetrically, by the following equations:

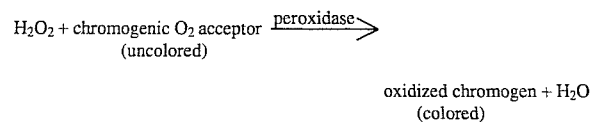

A glucose analyzer, available from NOVA Biomedical, amperometrically measures the production of $H_2O_2$ by oxidation of the $H_2O_2$ on a platinum electrode. Further details are provided in the Examples, below. In any event, the preferred analytical technique is capable of detecting changes in glucose concentration on the order of about 1–10 mg %.

There were 26 males and 16 females, age 29±5 years, none with preexisting disease. Initial glucose concentrations for the 42 normals averaged 96.7±19.1 mg % (range 65 to 179). For all samples, the decrease in glucose concentration during the three hours of measurement was practically linear, at an average rate of 9.79±1.85 mg % per hour (7.10–14.23) and regression coefficients of 0.97±0.03 (0.88–1.00). A representative study is shown in FIG. 1.

Consistent with previous literature (35), this linearity existed regardless of the initial glucose concentration. Parallel activated glycolysis rates of PMA stimulated blood averaged 12.14±2.21 mg % per hour (8.83 to 17.99). The increase in the rate of glucose consumed by whole blood containing neutrophils activated in vitro by PMA over that of basal (native) whole blood averaged 2.34±1.74 mg % per hour (−0.63 to 7.74).

Baseline glycolysis rates were found to be significantly related (p=0.03) to the red blood cell count, but not to any other cell line (e.g., p=0.7 for neutrophils). Glycolysis rates after PMA stimulation, however, were significantly related to the neutrophil count (p=0.049) as well as the RBC count (p=0.002). Surprisingly, although platelets are known to consume glucose and are stimulated by PMA, they did not appear to contribute significantly to either baseline or maximal rates.

Using the information obtained from the specimens of the normal volunteers, linear regression equations for predicted quiescent cell glycolysis rates (baseline values, $G_1$) and predicted activated cell glycolysis rates (values obtained after stimulation with PMA, $G_2$) were established, controlling for neutrophil and rbc counts.

$$\text{Basal Rate } (G_1) = 2.183 + (0.000102 * pmn) + (1.516 * rbc) \quad (1)$$

$$\text{Stimulated Rate } (G_2) = -1.759 + (0.000755 * pmn) + (2.354 * rbc) \quad (2)$$

Graphical analysis of the fit of our models revealed both relationships to have bell-shaped distributions of residuals, skewed slightly to the right. The standard errors of estimate for both models were approximately equal. To simplify the subsequent analysis, we therefore assumed an underlying normal residual distribution.

Each measured glycolysis rate (G), either with or without PMA, was placed on the spectrum between predicted basal ($G_1$) and predicted activated ($G_2$) rates by the LLR equation, with V $$LLR = [\{G - (G_1 + G_2)/2\} * \{G_2 - G_1\}] \div 3.256 \quad (3)$$

(the square of the standard error of estimate)=3.256. V was derived from the rates measured in normals. Log likelihood ratios for normal basal and PMA activated blood are shown in FIG. 2.

Furthermore, the difference between the LLR calculated for the basal glycolysis rate ($LLR_{basal}$) and that calculated for the stimulated glycolysis rate ($LLR_{stim}$) was used to indicate the magnitude of the response by the neutrophils to additional exogenous stimulation by PMA. This unitless number is referred to herein as the "delta value" or Δ.

The delta value for normals was found to be 1.83±1.72.

Thus, according to the method of the present invention, for a patient with a rbc count=4.5 and a neutrophil count= 9.579, the predicted basal glycolysis rate ($G_1$)=9.98 and predicted stimulated rate ($G_2$)=16.07. A measured basal glycolysis rate of 12.1 yields a $LLR_{basal}$ of −1.73. A measured stimulated glycolysis rate of 17.55 yields a $LLR_{stim}$ of 8.46. Hence, Delta Value=$LLR_{stim}-LLR_{basal}$=10.19.

Next, MICU patients, 22 male and 28 female, having an average age of 65±18 years (27 to 92), were studied. There were 16 patients who met the criteria for "non-sepsis," 15 for "sepsis," 19 for "severe sepsis" and 9 for "septic shock". (See the criteria set forth in Section 6.5, below.) Basal and activated glycolysis rates are shown in Table I. There were no septic deaths in the non-sepsis group, 8% (2/25) in the sepsis/severe sepsis group and 56% (5/9) in the septic shock group. In the sepsis/severe sepsis group, 36% of patients had gram negative infections, 12% gram positive, 4% fungal and 48% culture negative. In the septic shock group, 45% of patients had gram negative infections, 11% gram positive and 44% were culture negative.

Predicted glycolysis rates, log likelihood ratios and delta values for normals, non-sepsis ICU patients, sepsis/severe sepsis patients and septic shock patients are shown in Table I. Comparison of the four groups showed a highly significant difference in the delta values between the sepsis/severe sepsis patients and all the other patients combined ($F_{3,87}$=11.986, p<0.0005). The delta values for the sepsis/severe sepsis group were significantly higher than those of the normal and septic shock groups ($F_{1,87}$=16.023, p<0.0005), but not significantly higher than the non-sepsis ICU patients. There was no significant difference between the control group and the septic shock group ($F_{1,87}$=0.038, p=0.85).

Correlation coefficients for neutrophil count versus delta value were calculated. The correlation increased steadily from 0.34 for the control group, 0.58 for the non-sepsis group, and 0.64 for the sepsis/severe sepsis group, but was only 0.13 for the septic shock group.

Because hemorrhage/transfusion has been shown to prime and activate neutrophils, the non-sepsis patient group was subdivided into those patients with gastrointestinal (GI) hemorrhage who received red blood cell transfusion and those who did not. Patients with hemorrhage/transfusion (n=4) had a delta value of 9.20±5.03, whereas those who did not (n=12) gave a delta value of 6.16±4.95 (p=0.3). Thus, the delta value, within patient categories, can be taken as a further indication of a patient precondition that may contribute to neutrophil activation in that patient.

5.5. Further Discussions

The present study shows that the rate of in vitro glycolysis by a sample of whole blood, and the amount by which this rate increases upon the addition of the neutrophil stimulator PMA, provides a qualitative index of neutrophil metabolic state. The determination of this index, referred to herein as the delta value, requires only red blood cell and neutrophil counts and measurement of glucose concentration in two tubes of blood (one containing native whole blood and another containing exogenous neutrophil stimulant) over time. These measurements are universally available, rapid, simple to perform and reproducible. Calculation of the delta value from these measurements is done by three simple equations, provided above.

Based on all 92 studies (42 controls and 50 patients), an average basal rate of 9.71±3.25 mg % per hour was found, a value consistent with the results obtained by others. A statistically significant difference between basal glycolysis rates between the four groups listed in Table I was not found. Thus, the basal glycolysis rates, by themselves, do not reflect neutrophil metabolism.

Significantly, however, these studies indicate that in vitro glycolysis measurements, used in conjunction with the mathematical relationships provided herewith, do provide a reliable indicator of neutrophil metabolic state. Furthermore, the predictive power of the present method has been confirmed by a comparison of the results obtained with the delta assay and known but more complex techniques. In particular, the states of neutrophil activity in a patient with sepsis and in a patient in septic shock, as predicted by the delta assay, are identical to those shown by ROS production. Moreover, delta values of patients with sepsis/severe sepsis are markedly higher than normals, indicating the presence of a large number of primed neutrophils that "burst" upon the addition of an exogenous neutrophil stimulant, such as PMA. The present study has also shown that delta values of patients in septic shock remain essentially the same as normals, suggesting the presence of either normally functioning neutrophils or suppressed neutrophils unresponsive to further exogenous stimulation.

It has also been found that delta values in critically ill patients with non-sepsis diagnoses are also statistically higher than normals. Without wishing to be limited by theory, a possible explanation might be that the neutrophils of some of these patients have been primed for reasons other than sepsis. For example, although awaiting further statistically confirmation, the small subgroup of patients who had GI hemorrhage and received red blood transfusions had average delta values higher than the nonsepsis group overall. These observations are thus consistent with previous studies showing that hemorrhage/transfusion can activate neutrophils (19).

In the present study, serial assays in the two septic shock patients who survived provided inconsistent results. The first patient had a high delta value that returned to normal over ten days, suggesting that although clinically the patient was in septic shock, his neutrophil metabolism resembled that of a patient with sepsis/severe sepsis. The second patient had a low delta value that did not follow a consistent course over five days. It is possible that serial measurements spread over a greater period of time may have more meaning than daily measurements.

Of the patients studied, three who were at risk for ARDS later progressed to develop ARDS. All three were classified in the sepsis/severe sepsis category. One patient had a low delta value. The other two patients had an average delta value of 12.58, much higher than the 8.46 average for the sepsis/severe sepsis group, as a whole. These findings suggest that perhaps higher delta values, reflecting highly charged or primed neutrophils, may have a role in predicting which "at risk" patients will progress to ARDS. In fact, within a given group of patients, the present method provides an indication of which patients are likely to be "at risk" of suffering from the onset of a neutrophil-mediated host autoinjury.

The present studies have also shown that the disclosed delta assay is not merely serving as a proxy for the neutrophil count. As discussed above, the neutrophil count, as part of the log likelihood ratio equation, is mathematically linked to the delta calculation. Additionally, the rate of glycolysis depends on the neutrophil count. However, although the correlation between delta value and neutrophil count increases from control through sepsis/severe sepsis, there was virtually no correlation in the septic shock group. The delta value, therefore, remains an index indicative of neutrophil metabolism which is distinct from the neutrophil count alone.

In summary, the present studies offer early detection of primed neutrophils in vitro using techniques that are universally available. In addition, the present methods can be performed using whole blood, thus obviating the need for preparing purified neutrophil isolates or the use of sophisticated equipment. Moreover, no highly specialized training is required of personnel to allow them to screen patients at epidemiologic risk for developing ARDS, MSOF, or the like. According to the present results, high delta values may provide an early marker of patients who will go on to develop a neutrophil-mediated host autoinjury, such as ARDS.

What is more, the present methods are useful in the design and monitoring of treatment studies. For instance, many specific anti-neutrophil binding therapies have been shown to prevent neutrophil associated injury in animal models (4). These therapies may include the administration of antibodies, including $IB_4$, a monoclonal antibody against the neutrophil CD18 adhesion glycoprotein complex, monoclonal antibodies directed against intracellular adhesion molecule I (ICAM-1) or E-selectin, pentoxifylline, adenosine and dapsone. With the simple and rapid methods disclosed, patients with primed neutrophils can be readily detected and specific therapies can be initiated. Other inhibitors of respiratory burst toxic products are listed in Table II, below.

Indeed, the practice of the present invention may avoid the need to treat large numbers of "at risk" patients in a shotgun approach, as occurred in a recent HA-IA study (45), to find instead those few who may benefit from the particular treatment regimen.

TABLE I

Predicted and measured data for four groups.

|  | Controls (n = 42) | Non-Sepsis (n = 16) | Sepsis/Severe Sepsis (n = 25) | Septic Shock (n = 9) |
|---|---|---|---|---|
| Age | 29 ± 5 | 53 ± 20 | 54 ± 29 | 65 ± 26 |
| Sex (M/F) | (26/16) | (8/8) | (8/17) | (6/3) |
| Apache II | — | 15 ± 16 | 20 ± 10 | 29 ± 5 |
| Neutrophils | 3.491 ± 0.806 | 7.945 ± 2.638 | 11.402 ± 4.927 | 8.706 ± 8.924 |
| RBC | 4.786 ± 0.43 | 3.733 ± 0.874 | 3.552 ± 0.789 | 3.378 ± 0.774 |
| G1 (Predicted) | 9.795 ± 0.680 | 8.659 ± 1.302 | 8.732 ± 1.293 | 8.193 ± 1.358 |
| G2 (Predicted) | 12.142 ± 1.319 | 13.068 ± 2.626 | 15.214 ± 4.141 | 12.768 ± 6.676 |
| RateBasal (Measured) | 9.795 ± 1.854 | 9.848 ± 4.828 | 9.849 ± 3.241 | 8.656 ± 5.213 |
| RateStim (Measured) | 12.142 ± 2.228 | 14.435 ± 5.198 | 13.738 ± 3.356 | 10.236 ± 4.737 |
| LLRBasal | −0.94 ± 1.40 | −2.77 ± 6.43 | −5.81 ± 11.66 | −1.67 ± 5.42 |
| LLRStim | 0.94 ± 1.60 | 4.17 ± 5.07 | 2.65 ± 8.27 | 0.51 ± 3.20 |
| DELTA VALUE | 1.83 ± 1.72 | 6.94 ± 4.99 | 8.46 ± 7.76 | 2.18 ± 3.16 |

TABLE II

Agents that inhibit the products of the respiratory burst.

Inhibitors of Neutrophil Function

Pentoxifylline
Adenosine
Aminophylline
Terbutaline
Dibutyryl-cAMP
Caffeine
Forskolin
Inhibitors of Adhesion Interleukin-4
Interleukin-8
Transforming growth factor-$\beta_1$
Monoclonal antibodies to adhesion molecules
Inhibitors of Degranulation Dapsone
Antioxidants Superoxide dismutase
Catalase
Glutathione
Vasoactive intestinal peptide TABLE II-continued Agents that inhibit the products of the respiratory burst.

Allopurinol
Oxypurinol
Pterin aldehyde
Heavy Metal Chelators

Deferoxamine
Apolactoferrin
Lactoferrin
Ceruloplasmin
U74500
Pyridoxal benzoyl hydrazone Citrate
Oxygen Radical Scavengers N-acetylcysteine
Mannitol
Ethanol
Dimethyl sulfoxide
Dimethyliourea
Uric acid
Vitamin E
Vitamin C TABLE II-continued Agents that inhibit the products of the respiratory burst.

Protease Inhibitors

Soybean tripsin inhibitor
$\alpha_1$-antiprotease
Phenylmethylsulfonyl fluoride
N-α-p-tosyl-1-lysine chloromethyl ketone
L-1-tosylamide-2-phenylethyl chloromethyl ketone
N-α-p-tosyl-L-arginine methyl ester hydrochloride
Eglin C
Secretory leukoprotease inhibitor cAMP, adenosine-3',5'-cyclic phosphate

6. CLINICAL STUDIES

6.1. Patient Consent

This study was approved by the Mt. Sinai Medical Center Institutional Review Board (IRB). In most patients, verbal consent was obtained from each participant. In septic obtunded ICU patients with no consenter available, the IRB approved waiver of consent for blood drawing. Any reference cited anywhere in this disclosure should be considered as being incorporated by reference herein in its entirety. A complete bibliography of all the references cited appears at the end of the description, just before the claims.

6.2. Granulocyte Reactive Oxygen Species (ROS) Formation Detected by DCFH-DA Fluorescence To determine conditions under which granulocytes in whole blood specimens could be activated by the addition of a granulocyte agonist (phorbol myristate 13-acetate (PMA), a direct activator of protein kinase C), 2', 7'-dichlorofluorescein diacetate (DCFH-DA) was used to detect the stimulation of reactive oxygen species (ROS) formation in pmn isolated from blood samples incubated with varying concentrations of PMA (11,46).

Four ml of venous blood obtained from normal volunteers (n=3) were drawn into heparinized tubes containing DCFH-DA to give a final concentration of DCFH-DA of 100 μm. The contents of the tubes were incubated for 15 minutes (47). One ml aliquots were then withdrawn from the tubes and incubated with varying concentrations of PMA (0, 50, 100, 500 ng/ml; Sigma Co., St. Louis) for an additional 15 minutes. All incubations were carried out at 37° C. under light shielding. Granulocytes were then separated by Histopaque density centrifugation, washed in Hank's buffered salt solution (Gibco/BRL Inc., Grand Island, N.Y.) containing 100 μg/ml propridium iodide (PI, Sigma), and resuspended in phosphate buffered saline with 1% formaldehyde. Percent fluorescence and mean channel shift were determined by flow cytometry (Coulter Inc., Hialeah, Fla.), gating on the major granular PI positive cell population. It was found that 100 ng/ml of PMA was sufficient to stimulate maximally the neutrophils present in the blood sample. All subsequent experiments were carried out using this concentration of exogenous stimulant.

6.3. Whole Blood Glucose Measurements

After blood drawing, glucose measurements were made within the first 10 minutes of blood drawing, then every 30 minutes for 180 to 240 minutes. Between measurements, the blood was incubated at ambient temperature and allowed to sediment. For each measurement, the sample was mixed and then pipetted by plastic pipette into a plastic cuvette. Blood that remained in the cuvette after a glucose measurement was pipetted back into the glass tube for incubation.

Whole blood glucose measurements were performed on a Stat Profile 5 glucose analyzer (NOVA Biomedical, Waltham, Mass., 02254). This glucose analyzer consists of a membrane containing immobilized glucose oxidase fitted onto a platinum anode. Glucose oxidase converts glucose, $O_2$, and $H_2O$ into gluconate, $H^+$, and hydrogen peroxide. The hydrogen peroxide produced is then oxidized at the platinum anode, generating a current proportional to the glucose concentration in the sample.

6.4. Determination of Glycolysis Rates for Normal Blood: Basal Rate and "Activated Neutrophils" or "Stimulated" Rate Eight ml of peripheral venous blood was drawn percutaneously from healthy adult volunteers. Blood was divided equally into a heparinized glass Vacutainer tube and a heparinized Vacutainer tube containing 100 ng/ml of PMA, gently mixed, and glucose measurements were made as described above. Simultaneous blood samples were sent to the clinical laboratory for complete blood count and cell differential, i.e., differentiation of the patient white blood cells made up of, for example, lymphocytes, neutrophils, monocytes, eosinophils, basophils, etc.

6.5. Prospective Evaluation of Medical Intensive Care Unit (MICU) Patients

Eight ml of blood were aseptically drawn either through an indwelling arterial catheter, a central venous catheter or from a peripheral vein. Simultaneous blood samples were sent to the clinical laboratory for complete blood count and differential. Glycolysis measurements were made as described above.

The following clinical definitions were applied for the 24-hour period before blood was drawn for the glycolysis assay.

Patients meeting any of the following definitions were labeled 'sepsis' for the purposes of this study. Definitions for sepsis, severe sepsis and septic shock in association with infection were used according to the ACCP/SCCM Consensus Conference Statement (36). Sepsis required two or more of the following symptoms: (1) temperature >38° C. or <36° C.; (2) heart rate>90 beats per minute; (3) respiratory rate>20 breathes per minute or $PaCO_2$<32 mm Hg; and (4) white blood cell count>12,000/cu mm, <4,000/cu mm, or >10% immature (band) forms. Severe sepsis was sepsis with evidence of peripheral hypoperfusion, including either lactic acidosis, oliguria or an acute alteration in mental status. Septic shock was sepsis with hypotension (systolic pressure 90 mm Hg or a reduction of ≧40 mm Hg from baseline) despite adequate fluid resuscitation, or the requirement of vasopressors.

Adult Respiratory Distress Syndrome (ARDS) was diagnosed if all off the following criteria were met (37): (1) acute respiratory failure requiring mechanical ventilation, (2) bilateral pulmonary infiltrates on chest radiograph, (3) pulmonary capillary wedge pressure of <18 mm Hg, (4) static pulmonary compliance 50 ml/cm $H_2O$, (5) arterial to alveolar partial pressure of oxygen ratio <0.25.

Patients in the MICU who did not meet the above criteria were labelled "non-sepsis."

6.6. Comparative Confirmation Studies

Two patients were assessed simultaneous for neutrophil metabolic state by using both in vitro glycolysis measurement and flow cytometry-measured ROS production (See, FIG. 4). This comparison was performed to confirm whether or not the delta assay described herein provides qualitatively similar information to that determined by a standard measure of neutrophil metabolism as reflected by ROS production.

The first patient (top panel of FIG. 4) was an 81 year old woman in septic shock. By flow cytometry, it was shown that her neutrophils were already activated before the addition of PMA. Hence, no increase with PMA stimulation was observed. The results for mean channel shift were 1.098 vs. 1.336 and for percent fluorescence, 20.0% vs. 33.1%. These values compare to results from normal control mean channel shift of 0.287 vs. 5.77 and percent fluorescence of 2.6% vs. 89 5% respectively This 81 year old patient's delta value was 2.88, compared to a normal control delta value of 3.13.

The second patient (bottom panel of FIG. 4) was a 53 year old man with sepsis. By flow cytometry his neutrophils showed a tremendous response to PMA, suggesting a large number of primed cells (mean channel shift, 2.34 vs. 119.6; percent fluorescence, 7.4% vs. 92.8%; normal control mean channel 2.382 vs. 21.82; percent fluorescence 3.6% vs. 31.15). This patient's delta value was 8.40, compared to a normal control of 3.52.

These results confirm the utility of the present method to serve as a predictor of patient neutrophil activity. It also illustrates the gross difference between the complexity associated with available "specialized" techniques that require sophisticated equipment and training and require calibration with a "normals" measurement for each analytical data point. In contrast, the delta assay disclosed herein uses relatively "simple" in vitro glycolysis measurements coupled to cell count measurements for which "normal" responses are not required for each and every measurement. The disclosed method is thus much easier to perform, is less tedious, and has more widespread applicability than traditional methods.

6.7. ARDS Patients

Three patients, who, based on previous clinical studies, were at epidemiologic risk for ARDS, had glycolysis assays performed and subsequently developed ARDS by the above criteria within the next 24 hours. The first was a 71 year old woman with pancreatitis in sepsis/severe sepsis with a delta value of 2.11. This patient later died of MSOF. Her low delta value may reflect a suppressed state of neutrophil activity, which may have resulted from her pancreatitis, more consistent with septic shock rather than sepsis/severe sepsis.

The second was a 26 year old man in the sepsis group with pulmonary septic emboli and a delta value of 9.03. The third was a 46 year old woman in the sepsis group with a delta value of 16.09. Though requiring further statistical confirmation in a larger study group (current p=0.88 relative to the sepsis/severe sepsis group), the last two patients in the sepsis/severe sepsis group (ave delta=12.58) who went on to develop ARDS had delta values higher than the 8.46 average obtained from the twenty-six patients grouped into the sepsis/severe sepsis category (see, FIG. 3). The results indicate, nevertheless, that a delta value above the average found for a given group of patients may be indicative of the greater propensity of a particular patient to develop a neutrophil-mediated host autoinjury.

It should be evident that other embodiments of the present invention would be apparent to those of ordinary skill in the art in view of the foregoing disclosure. Such embodiments, though not specifically disclosed herein, are nonetheless considered to be within the scope and spirit of the present invention, which should not be construed as limited by the particular examples described herein but only by the claims that follow.

Bibliography:

1. Zimmerman J. J., Shelhamer J. H., Parrillo J. E. Quantitative analysis of polymorphonuclear leukocyte superoxide anion generation in critically ill children. *Crit Care Med* 1985; 13:143–150.
2. Zimmerman J. J., Millard J. R., Farrin-Rusk C. Septic plasma suppresses superoxide anion synthesis by normal homologous polymorphonuclear leukocytes. *Crit Care Med* 1989; 17:1241–1246.
3. Zimmerman J. J., Ringer T. V. Inflammatory host responses in sepsis. *Crit Care Clinics* 1992; 8:163–189.
4. Bone R. C. Inhibitors of complement and neutrophils: a critical evaluation of their role in the treatment of sepsis. *Crit Care Med* 1992; 20:891–898.
5. Zimmerman J. J. Polymorphonuclear leukocytes-agents of host defense and autoinjury. In: Shoemaker, W. ed. *Textbook of Critical Care*. Philadelphia, Pa.: W. B. Saunders Company; 1989:969–976.
6. Nuijens J. H., Abbink J. J., Wachtfogel Y. T., Colman R. W., Eerenberg A. J., Dors D., Kamp A. J., Strack van Schijndel R. J., Thijs L. G., Hack C. E. Plasma elastase alpha 1-antitrypsin and lactoferrin in sepsis: evidence for neutrophils as mediators of fatal sepsis. *J Lab Clin Med* 1992; 119:159–68.
7. Fein A. M., Grant M. M., Niederman M. S., Kantrowitz N. Neutrophil-endothelial cell interaction in critical illness. *Chest* 1991; 99:1456–62.
8. Rothe G., Kellermann W., Valet G. Flow cytometric parameters of neutrophil function as early indicators of sepsis- or trauma-related pulmonary or cardiovascular organ failure. *J Lab Clin Med* 1990; 115:52–61.
9. Tennenberg S. D., Solomkin J. S. Neutrophil activation in sepsis. *Arch Surg* 1988; 123:171–175.
10. Zimmerman G. A., Renzetti A. D., Hill H. H. Functional and metabolic activity of granulocytes from patients with adult respiratory distress syndrome. *Am Rev Resp Dis* 1983; 127:290–300.
11. Chollet-Martin S., Montravers P., Gibert C., et al. Subpopulations of hyperresponsive polymorphonuclear neutrophils in patients with adult respiratory distress syndrome. *Am Rev Respir Dis* 1992; 146:990–996.
12. Rivkind A. I., Siegel J. H., Littleton M., De Gaetano A., Mamantov T., Laghi F., Stoklosa J. C. Neutrophil oxidative burst activation and the pattern of respiratory physiologic abnormalities in the fulminant post-traumatic adult respiratory distress syndrome. *Circ-Shock* 1991; 33:48–62.
13. Shasby D. M., Vanbenthuysen K. M., Tate R. M., Shasby S. S., McMurtry I., Repine J. E. Granulocytes mediate acute edematous lung injury in rabbits and in isolated rabbit lungs perfused with phorbol myristate acetate: Role of oxygen radicals. *Am Rev Resp Dis* 1982; 125:443–447.
14. Anderson B. O., Harken A. H. Multiple organ failure: inflammatory priming and activation sequences promote autologous tissue injury. *J Trauma* 1990; 30:S44–S49.
15. Vedder N. B., Winn R. K., Rice C. L., Harlan J. M. Neutrophil-mediated vascular injury in shock and multiple organ failure. *Prog Clin Biol Res* 1989; 299:181–91.
16. Goris R. J. Mediators of multiple organ failure. *Intensive Care Med* 1990; 16:S192–196.
17. Van Bebber I. P., Boekholz W. K., Goris R. J., Schillings P. H., Dinges H. P., Bahrami S., Redl H., Schlag G. Neutrophil function and lipid peroxidation in a rat model of multiple organ failure. *J Surg Res* 1989; 47:471–5.
18. Welbourn C. R. B., Goldman G., Paterson I. S., Valeri C. R., Shepro D., Hechtman H. B. Pathophysiology of ischaemia reperfusion injury: central role of the neutrophil. *Br J Surg* 1991; 78:651–655.
19. Barroso-Aranda J., Schmid-Schönbein G. W. Transformation of neutrophils as indicator of irreversibility in hemorrhagic shock. *Am J Physiol* 1989; 257 (Heart Circ. Physiol 26):H846–H852.
20. Babior B. M. Oxygen-dependent microbial killing by phagocytes. *NEJM* 1978; 298:659–668.
21. DeChatelet L. R., Lees C. J., Walsh C. E., Long G. D., Shirley P. S. Comparison of the calcium ionophore and phorbol myristate acetate on the initiation of the respiratory burst in human neutrophils. *Infect Immun* 1982; 38:969–974.
22. Sbarra A. J., Karnovsky. The biochemical basis of phagocytosis. I. Metabolic changes during the ingestion of particles by polymorphonuclear leukocytes. *J Biol Chem* 1959; 234:1355–1362.
23. Vespasiano M. C., Lewandoski J. R., Zimmerman J. J. Longitudinal analysis of neutrophil superoxide anion generation in patients with septic shock. *Crit Care Med* 1993; 21:666–672.
24. Allen R. C., Stevens D. L. The circulating phagocyte reflects the in vivo state of immune defense. *Curr Opin Infect Dis* 1992; 5:389–98.

25. Wollert P. S., Menconi M. J., O'Sullivan B. P., Wang H., Larkin V., Fink M. P. LY255283, a novel leukotriene $B_4$ antagonist, limits activation of neutrophils and prevents acute lung injury induced by endotoxin in pigs. *Surgery* 1993; 114:191–8.

26. Falcon-Lesses M. Glycolysis in normal and leukemic blood. *Arch Intern Med* 1927; 39:412–420.

27. Caraway W. T., Watts N. B. Carbohydrates. In: Teitz, N. W. ed. *Textbook of Clinical Chemistry*. Philadelphia: W. B. Saunders, 1986; 775–828.

28. Pane G. A., Epstein F. B. Glucose. *Emerg Med Clin N Amer* 1986; 4:193 205.

29. Horwitz D. L. Factitious and artifactual hypoglycemia. *Endocrin and Metab Clin North Am* 1989; 18:203–210.

30. Field J. B., Williams H. E. Artifactual hypoglycemia associated with leukemia. *N Engl J Med* 1961; 265:946–948.

31. Arem R., Jeang M. K., Blevens T. C., Waddell C. C., Field J. B. Polycythemia rubra vera and artifactual hypoglycemia. *Arch Intern Med* 1982; 142:2199–2201.

32. Billington C. J., Casciato D. A., Choquette D. L., Morley J. E. Artifactual hypoglycemia associated with polycythemia vera. *JAMA* 1983; 249:774–775.

33. Lefor A. T., Miller M. Factitious hypoglycemia associated with eosinophilic leukemoid reaction. *NY State J Med* 1985; 85:34–35.

34. Goodenow T. J., Malarkey W. B. Leukocytosis and artifactual hypoglycemia. *JAMA* 1977; 237:1961–1962.

35. Rawnsley H. M., Bowman H. M. Autoglycolysis in leukemic and nonleukemic blood. *Am J Med Sci* 1965; 249:203–210.

36. Bone R. C., Balk R. A., Cerra F. B., et. al. Definitions for sepsis and organ failure and guidelines for the use of innovative therapies in sepsis. *Chest* 1992; 101:1644–55.

37. Parsons P. E., Moore F. A., Moore E. E., Ikle D. N., Henson P. M., Worthen G. S. Studies on the role of tumor necrosis factor in adult respiratory distress syndrome. *Am Rev Resp Dis* 1992; 146:694–700.

38. Curnette J. T., Babior B. M. Metabolism of neutrophils. In: Williams W. J., Beuther E., Erslev A. J., Lichtman M. A. eds. *Hematology* New York: McGraw-Hill, Inc., 1990; 775–780.

39. Carson D. A., Kipps T. J. Biochemistry and function of lymphocytes. In: Williams, et al. pp 926–932.

40. Beuther E. Energy metabolism and maintenance of erythrocytes. In: Williams, et al. pp 355–368.

41. Tilton W. M., Seaman C., Carriero D., Piomelli S. Regulation of glycolysis in the erythrocyte: role of the lactate/pyruvate and NAD/NADH ratios. *J Lab Clin Med* 1991; 118:146–152.

42. Holmson H. Metabolism of platelets. In: Williams, et al. pp 1200–1233.

43. Weissman M., Klein B. Evaluation of glucose determinations in untreated serum samples. *Clin Chem* 1958; 4:420–422.

44. Sazama K., Robertson E. A., Chesler R. A. Is antiglycolysis required for routine glucose analysis? *Clin Chem* 1979; 25:2038–2039.

45. Luce J. M. Introduction of new technology into critical care practice: A history of HA-1A human monoclonal antibody against endotoxin. *Crit Care Med* 1993; 21:1233–1241.

46. Burrow S., Valet G. Flow cytometric characterization of stimulation, free radical formation, peroxidase activity and phagocytosis of human granulocytes with 2,7-dichlorofluorescein. *Eur J Cell Biol* 1987; 43:128–138.

47. Himmelfarb J., Hakim R. M., Holbrook D. G., Leeber D. A., Ault K. A. Detection of granulocyte reactive oxygen species formation in whole blood using flow cytometry. *Cytometry* 1992; 13:83–89.

48. Sackett D. L., Haynes R. B., Tugwell P. Clinical epidemiology: A basic science for clinical medicine. Little, Brown & Co. Boston/Toronto 1985.

What is claimed is:

1. A method of determining a metabolic state of a patient's neutrophils comprising:

(a) measuring a patient's basal rate of glycolysis, red blood cell (rbc) count and neutrophil (pmn) count;

(b) relating the measured basal rate of glycolysis with said patient's predicted basal and predicted stimulated rates of glycolysis to provide a log likelihood ratio (LLR), which ratio is an indication of the metabolic state of said patient's neutrophils, said predicted basal and predicted stimulated rates of glycolysis being derived from separate relationships established, respectively, from measurement of basal and stimulated rates of glycolysis of a population of normal individuals as a function of their rbc and pmn counts.

2. A method of determining a metabolic state of a patient's neutrophils comprising:

(a) establishing a first relationship, which is predictive of a basal rate of glycolysis as a function of red blood cell (rbc) count and neutrophil (pmn) count, by measuring basal rates of glycolysis, rbc counts, and pmn counts of a population of normal individuals;

(b) establishing a second relationship, which is predictive of a stimulated rate of glycolysis as a function of rbc count and pmn count, by measuring stimulated rates of glycolysis, rbc counts, and pmn counts of a population of normal individuals whose neutrophils having been stimulated exogenously;

(c) measuring a patient's basal rate of glycolysis, rbc count and pmn count;

(d) calculating said patient's predicted basal and predicted stimulated glycolysis rates from said patient's rbc count and pmn count, using said first and second relationships, respectively;

(e) relating said patient's measured basal rate of glycolysis with said patient's predicted basal and predicted stimulated rates of glycolysis to provide a log likelihood ratio (LLR), which ratio is an indication of the metabolic state of said patient's neutrophils.

3. The method of claim 2 in which said patient's predicted basal rate of glycolysis, $G_1$, is derived from the relationship (1), given below:

$$\text{Basal Rate } (G_1) = C_1 + (a_1 * pmn) + (b_1 * rbc) \qquad (1)$$

in which pmn and rbc are the measured pmn and rbc counts, respectively, $C_1$ is a constant, and $a_1$ and $b_1$ are x-coefficients obtained from regression analysis.

4. The method of claim 2 in which said patient's predicted stimulated rate of glycolysis, $G_2$, is derived from the relationship (2), given below:

$$\text{Stimulated Rate } (G_2) = C_2 + (a_2 * pmn) + (b_2 * rbc) \qquad (2)$$

in which pmn and rbc are the measured pmn and rbc counts, respectively, $C_2$ is a constant, and $a_2$ and $b_2$ are x-coefficients obtained from regression analysis.

5. The method of claim 2 in which said LLR is derived from the relationship (3), given below:

$$LLR=[\{G-(G_1+G_2)/2\}*\{G_2-G_1\}]\div V \qquad (3)$$

in which G is the measured basal rate of glycolysis for said patient, $G_1$ is the predicted basal rate of glycolysis for said patient, $G_2$ is the predicted stimulated rate of glycolysis for said patient, and V is the square of the standard error of estimate.

6. A method of stratifying a population of patients according to a metabolic state of their neutrophils comprising:

(a) measuring a patient's basal and stimulated rates of glycolysis, red blood cell (rbc) count and neutrophil (pmn) count;

(b) relating the measured basal rate of glycolysis with said patient's predicted basal and predicted stimulated rates of glycolysis to provide a first log likelihood ratio ($LLR_{basal}$);

(c) relating said measured stimulated rate of glycolysis with said patient's predicted basal and predicted stimulated rates of glycolysis to provide a second log likelihood ratio ($LLR_{stim}$), said predicted basal and predicted stimulated rates of glycolysis being derived from separate relationships established, respectively, from the measurement of the basal and stimulated rates of glycolysis of a population of normal individuals as a function of their rbc counts and pmn counts;

(d) subtracting said $LLR_{basal}$ from said $LLR_{stim}$ to provide a delta score ($\Delta$), which is a measure of the propensity of the neutrophils of a given patient to undergo exogenous stimulation;

(e) classifying patients of a given patient population into patient subgroups according to their $\Delta$ scores, to provide a stratification of said population of patients according to the metabolic state of their neutrophils.

7. A method of predicting the propensity of a patient to suffer from a neutrophil-associated host autoinjury relative to a population of patients comprising:

(a) measuring a patient's basal and stimulated rates of glycolysis, red blood cell (rbc) count and neutrophil (pmn) count;

(b) calculating a predicted basal glycolysis rate, $G_1$, from a first relationship established by measuring basal rates of glycolysis, rbc counts, and pmn counts of a population of normal individuals;

(c) calculating the predicted stimulated glycolysis rate, $G_2$, from a second relationship established by measuring stimulated rates of glycolysis, rbc counts, and pmn counts of a population of normal individuals;

(d) determining a basal log likelihood ratio, $LLR_{basal}$, and stimulated log likelihood ratio, $LLR_{stim}$, from the measured basal and measured stimulated rates of glycolysis, respectively;

(e) obtaining a delta value or $\Delta$ score for the patient from the difference in the values of $LLR_{basal}$ and $LLR_{stim}$;

(f) comparing the patient's delta value or $\Delta$ score with an average of delta values obtained from a population of patients, a delta value that is higher than the average being taken as an indication of a higher propensity of the patient to suffer from a neutrophil-associated host autoinjury relative to the population of patients.

8. The method of claim 7 in which the average of delta values is obtained from a population of patients similarly at risk of suffering from a neutrophil-associated host autoinjury.

9. The method of claim 7 which further comprises stratifying patients into further subgroups according to the metabolic state of their neutrophils within categories of normals, non-sepsis, sepsis/severe sepsis, and patients in septic shock.

10. The method of claim 9 which further comprises identifying those patient subgroups to be given treatment regimens specific to those patient subgroups.

11. The method of claim 10 in which the treatment regimen is directed to prevention or alleviation of neutrophil-mediated host autoinjury.

12. The method of claim 10 in which the treatment regimen is directed to treatment of sepsis or septic shock.

13. The method of claim 10 in which the treatment regimen is directed to prevention or alleviation of adult respiratory distress syndrome (ARDS).

14. The method of claim 10 in which the treatment regimen is directed to prevention or alleviation of multiple systems organ failure (MSOF).

15. The method of claim 10 in which the treatment regimen is directed to prevention or alleviation of reperfusion injury.

16. The method of claim 10 in which the treatment regimen is directed to prevention or alleviation of hemorrhagic shock.

17. The method of claim 10 in which the treatment regimen is directed to prevention or alleviation of acute lung injury.

18. The method of claim 10 in which the treatment regimen includes administration of an antibody.

19. The method of claim 10 in which the treatment regimen includes administration of an agent that inhibits the products of neutrophil respiratory burst.

20. The method of claim 7 which further comprises monitoring subsequent changes in said $\Delta$ scores, which changes offer an indication of efficacy or lack thereof of a treatment regimen.

21. The method of claim 7 which further comprises monitoring subsequent changes in said $\Delta$ scores, which changes offer an indication of responsiveness or changes in condition of individuals subjected to a treatment regimen.

22. An apparatus for determining a metabolic state of a patient's neutrophils comprising:

(a) a sensor for taking single or multiple measurements of a patient's blood glucose;

(b) a sensor for measuring a patient's rbc count;

(c) a sensor for measuring a patient's pmn count;

(d) a processor for correlating a patient's measured glycolysis rate, rbc count, and pmn count to obtain a log likelihood ratio (LLR).

23. The apparatus of claim 22 which is equipped with a processor for calculating a delta value ($\Delta$) from $LLR_{stim}$ and $LLR_{basal}$ which are the log likelihood ratios obtained from measured stimulated glycolysis and measured basal glycolysis rates, respectively.

24. The apparatus of claim 22 which performs said patient's blood glucose measurements automatically.

25. The apparatus of claim 22 which can perform analyses on more than one blood sample.

26. The apparatus of claim 25 which performs substantially simultaneous analyses on a native blood sample and an exogenously stimulated blood sample.

27. The apparatus of claim 26 which is equipped with adding and mixing means for introduction of at least one reagent to a blood sample for exogenous stimulation of same.

28. The apparatus of claim 26 in which said at least one reagent is phorbol myristate 13-acetate (PMA).

* * * * *